US011877758B2

(12) United States Patent
Calvo

(10) Patent No.: US 11,877,758 B2
(45) Date of Patent: Jan. 23, 2024

(54) RELEASE SYSTEM AND CUTTING PROFILE APPLIED TO DISPOSABLE SELF-LOCKING INTRACRANIAL DRILL BIT

(71) Applicant: Antonio Martos Calvo, Diadema (BR)

(72) Inventor: Antonio Martos Calvo, Diadema (BR)

(*) Notice: Subject to any disclaimer, the term of this patent is extended or adjusted under 35 U.S.C. 154(b) by 27 days.

(21) Appl. No.: 17/362,768

(22) Filed: Jun. 29, 2021

(65) Prior Publication Data
US 2022/0410353 A1   Dec. 29, 2022

(51) Int. Cl.
*A61B 17/16* (2006.01)
*A61B 90/00* (2016.01)

(52) U.S. Cl.
CPC ....... *A61B 17/1695* (2013.01); *A61B 2090/08021* (2016.02)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1662; A61B 17/1695
See application file for complete search history.

(56) References Cited

U.S. PATENT DOCUMENTS

| | | | | |
|---|---|---|---|---|
| 11,154,310 B2 * | 10/2021 | Collerais | ............ | A61B 17/1695 |
| 2009/0024129 A1 * | 1/2009 | Gordon | ............... | A61B 17/1617 606/180 |
| 2017/0027594 A1 * | 2/2017 | Ujvari | ................ | A61B 17/1617 |
| 2019/0142439 A1 * | 5/2019 | Collerais | ............ | A61B 17/1617 606/80 |
| 2022/0410353 A1 * | 12/2022 | Calvo | ................ | A61B 17/1695 |

FOREIGN PATENT DOCUMENTS

| | | | | |
|---|---|---|---|---|
| BR | 112021002582 A2 * | 5/2021 | ......... | A61B 17/1617 |
| BR | 202019026790 U2 * | 6/2021 | ......... | A61B 17/1695 |
| CN | 112533549 A * | 3/2021 | ......... | A61B 17/1617 |
| CN | 113693669 A * | 11/2021 | | |
| CN | 115426978 A * | 12/2022 | ........... | A61B 17/162 |
| DE | 102020110918 A1 * | 10/2021 | ........... | A61B 17/162 |
| EP | 3287083 A1 * | 2/2018 | ........... | A61B 17/162 |
| GB | 2597512 A * | 2/2022 | ......... | A61B 17/1695 |

(Continued)

*Primary Examiner* — Eric S Gibson
(74) *Attorney, Agent, or Firm* — Heslin Rothenberg Farley & Mesiti PC

(57) ABSTRACT

Release System and Cutting Profile applied to disposable self-locking intracranial drill bit, comprising a disposable cranial drill bit, for single-use, assembled from a coupling mechanism with an internal drill bit and another external one, where an axial load is applied to the cutting edges to transmit the rotary movement to the device, so that, after accessing the cranial bone the mechanism is released and the drill bit ceases its movement, being the coupling mechanism composed by a mechanical arrangement of two sliding helical cams, which interact with a ring, the geometry of which results in coupling, when the drill bit contacts the cranial bone surface, and the drill bit release, once the internal drill bit crossed the bone without affecting the lower cranial layers. The set is encapsulated in a plastic body, which allows the drill bit assembly in a number of craniotomy equipment.

4 Claims, 15 Drawing Sheets

(56) References Cited

FOREIGN PATENT DOCUMENTS

| WO | WO-2015150844 A1 | * | 10/2015 | ......... A61B 17/1617 |
|----|------------------|---|---------|------------------------|
| WO | WO-2016059608 A1 | * | 4/2016  | ......... A61B 17/1633 |
| WO | WO-2020035709 A1 | * | 2/2020  | ......... A61B 17/1617 |
| WO | WO-2021198418 A1 | * | 10/2021 | ......... A61B 17/1695 |
| WO | WO-2021214026 A2 | * | 10/2021 | ........... A61B 17/162 |

* cited by examiner

G-G

Fig. 8
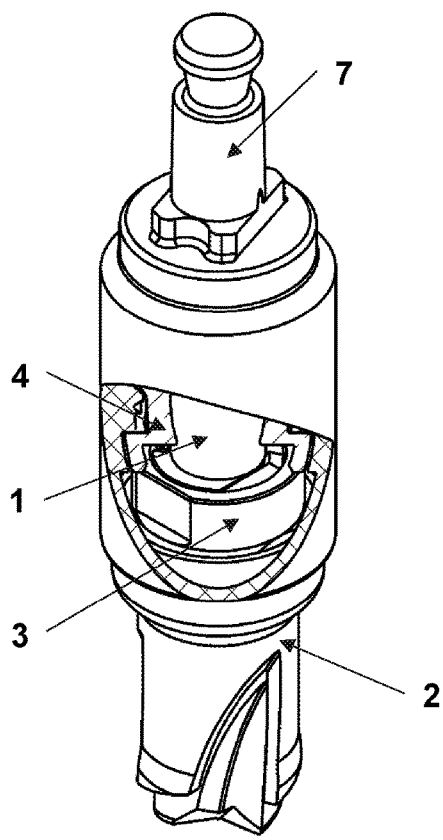
Fig. 9
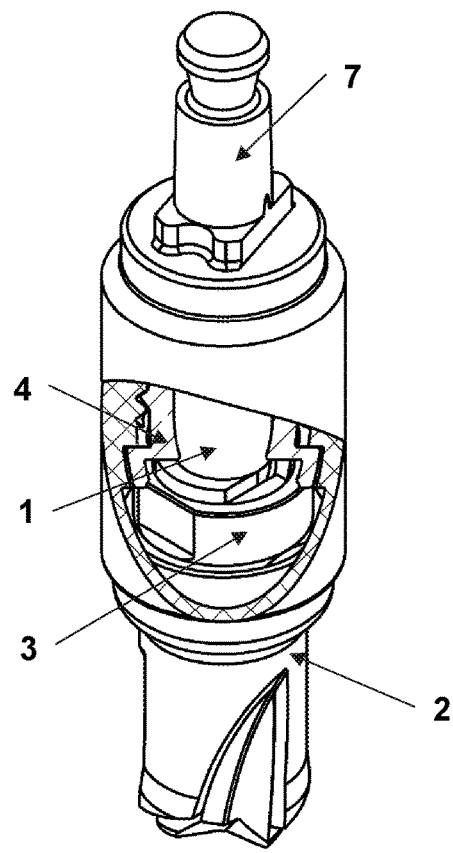
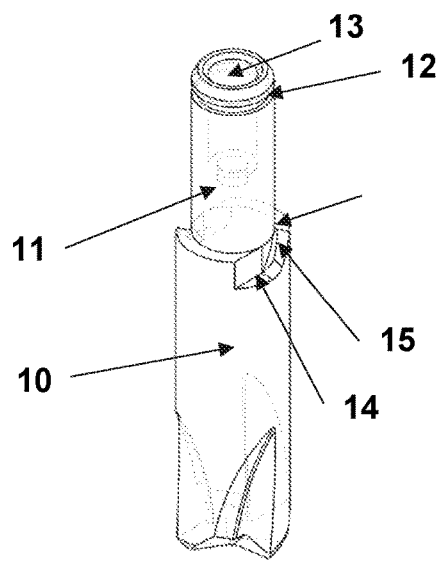
Fig. 10
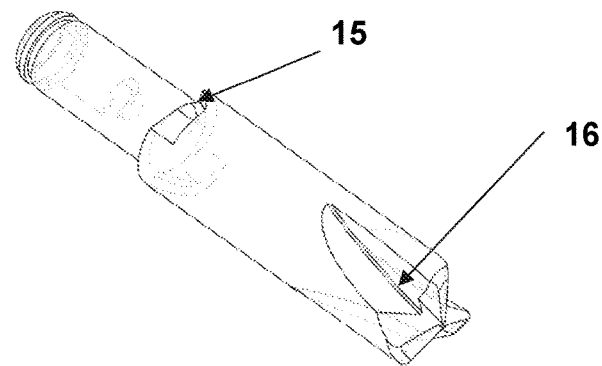
Fig. 11 det. x det. y

RELEASE SYSTEM AND CUTTING PROFILE APPLIED TO DISPOSABLE SELF-LOCKING INTRACRANIAL DRILL BIT

Cranial surgery procedures, in general, require access to the brain structures. For this purpose, it's necessary to drill holes through the cranial bone so as to access to the neurosurgeon's areas of interest. During the drilling process, the lower layers, such as the meninx or the brain itself, must be preserved.

STATE-OF-THE-ART REFERENCES

U.S. Pat. No. 2,842,131
U.S. Pat. No. 4,362,161
U.S. Pat. No. 4,319,577
U.S. Pat. No. 4,699,550
U.S. Pat. No. 4,884,571
EPO EP2 022 414 A1
U.S. Pat. No. 4,456,010
U.S. Pat. No. 4,830,001
U.S. Pat. No. 5,380,333

OTHER PUBLICATIONS

Acra-cut, Inc. Brochure "Disposable Cranial Perforators" Acra-cut, Inc., 1989 Main Street, Acton, Massachusetts 01720.
Acra Cut Product Brochure by Acra Cut, Inc. of Acton Massachusetts 1999.

This patent object is manufactured with materials allowing, if applicable, its sterilization under high temperatures and is used to allow the surgical access to brain tumors, biopsies, hematoma drainage, encephalic cyst aspiration, implantation of interstitial and intracavitary radioactive isotopes, implantation of stimulation electrodes, endoscopy, radiosurgery and other surgical interventions in the cranial region where their determination and precise access is crucial.

It's a double-acting drill bit, with coaxial operation, to be used with a surgical drilling machine.

What is known in the state-of-the art, are drill bits for similar application, but are manufacture under a complex design, being also complex parts, with high operational cost. In case of reuse, the state-of-the-art drill bits are manufactured in such a way that the maintenance and/or cleaning of the set following use is very difficult.

Intracranial surgeries frequently comprise the introduction of an electrode or cannula into the brain so as to reach the affected region and, then, proceed with the appropriate procedure. In this case, we will not mention the second part of the surgery, because it's not important for the proposal claimed at the moment.

To have access to the patient's brain using cannulas and/or electrodes, just the skull drilling by using a drill bit is required to insert the instruments.

There are cranial drillers which allow the drill bit to be rotated only when the drill bit is submitted to an axial load with the desired magnitude. After the load is eliminated or is below a certain pre-determined limit, the drill bit rotation ceases. Such devices, which use a coupling mechanism allowing a driver to be coupled only with sufficient axial load, are disclosed in U.S. Pat. Nos. 2,842,131; 4,362,161; 4,319,577; 4,884,571; and 4,699,550 and EPO EP 2 022 414 A1.

Other previous documents describe reusable drillers which allow the disassembly and assembly for the cleaning and sterilization process.

In this case, there's a risk that the drill bit is wrongly assembled and, consequently, comes to fail during the surgery, causing injuries or even the patient death. For this reason, disposable drill bits were developed and started to adopt a plastic body, keeping the mechanism protected and preventing or hindering its disassembly, as disclosed in documents U.S. Pat. Nos. 4,699,550; 4,456,010; 4,830,001; 5,380,333. Another disadvantage noted in already known cranial drill bits would be the larger number of components or complex geometries, requiring more expensive processes, which affect the final cost of the product. And, finally, the cutting areas noted in other drill bits are not able to reach large thickness bones.

SUMMARY OF THE INVENTION

In this disclosure we describe RELEASE SYSTEM AND CUTTING PROFILE APPLIED TO DISPOSABLE SELF-LOCKING INTRACRANIAL DRILL BIT comprising a cutting shaft (1) having a drill bit at one end and cams (14, 15 and 17) proximate to the other end, an external ring (3) having internal faces that interact with said cams (14, 15 and 17) and external surfaces (34), a bushing (4) (also referred to as a "dragging trigger") configured to fit within a spring-containing housing (7) and having internal surfaces (42, 43 and 44) configured to interact with surface (34) of the external ring wherein said cams on the cutting shaft comprise flat faced cams (14,17) and a helically faced cam (15) located between the flat faced cams (14, 17) and a dragging geometry is effected by opposed cams (14-34-43; 15-35; 36-44), configured to interact while the drill bit experiences resistance to forward movement and to disconnect when the drill bit experiences no resistance to forward movement, by the action of the spring [5] on the external ring thereby ending the connections between the cams (14, 15, 16) mounted on the cutting shat and the and the surfaces (34, 35,36) of the external ring and the cooperating internal surfaces of the bushing (42, 43 and 44).

In one embodiment, the cutting shaft comprises (1) an "internal cutting shaft", presenting two diameters, being that the largest diameter presents the cutting profile at one end and integrated cams proximate to the other end, the internal cutting shaft serving as a guide to the coupling and releasing mechanism; and (2) a secondary drill bit, called "external cutting body" is mounted with a threaded ring, which causes the interaction with the internal cutting shaft cams wherein. A retaining ring fixed to the smaller diameter of the internal cutting shaft, maintains the movement of the bushing.

The housing within which the spring is mounted may be a Hudson-type coupling made of plastic, where the entire set is assembled and sterilized.

The drill bit has a constructive variant, this being of greater length compared to the current drill bits. This resource allows the outside diameter of the external cutting body to be guided through stereotaxic equipment or surgical robots.

The proposed approach allows a single-use process, with improved safety and performance due to reduced moving parts.

This cranial drill bit contemplates a coupling system and cutting profile that are different to the currently existing ones, providing a single and exclusive performance.

BRIEF DESCRIPTION OF THE DRAWINGS

The system will be described according to the attached drawings, provided as follows:

FIGS. 1 to 9 refer to the general description of the set.

FIGS. 10 to 22 show the scope of the innovation herein.

FIGS. 21 to 23 refer to the detailed description of claim 2.

The set of figures is detailed as follows:

FIG. 1 shows the isometric view of the assembled drill bit;

FIG. 2 shows a "lone version" variant:

FIG. 3 shows the disassembled set in the "short version":

FIG. 4 shows the disassembled set in the "long version";

FIG. 5 shows the cross-sectional view of the drill bit, in the released condition;

FIG. 6 and its enlarged detail show the cross-sectional view of the drill bit, on the cranial bone;

FIG. 7 and its enlarged detail shows a cross-sectional view of the cam section, in the coupled condition during the drilling operation;

FIGS. 8 and 9 show the cam interaction with the external body ring in the released and coupled conditions, respectively.

FIGS. 10 and 11 show details of the internal cutting shaft, comprising a shaft with two diameters, being that the largest diameter presents the cutting profile in one end and two integrated cams in the other one, and the smallest diameter serves as a guide for the dragging trigger holed, so that it couples to the cam and transmits the rotary movement:

FIG. 12 shows the internal cutting shaft in its long construction variant:

FIG. 13 is the exploded view of the external cutting body, where the ring is threaded;

FIG. 14 corresponds to the exploded view of the external cutting body, in its constructive variant, with the external body ring:

FIG. 15 shows the isometric view of the external body ring and the protrusions which interact with the internal cutting shaft cam:

FIG. 16 shows the isometric view of the external cutting body ring assemble with the ring, forming a subset which interacts with the internal cutting shaft cams:

FIG. 17 shows the isometric view of the dragging trigger:

FIG. 18 shows a cross-sectional isometric view only of the coupling body and the dragging trigger, representing the set in the coupled condition;

FIG. 19 shows a cross-sectional isometric view only of the coupling body and the dragging trigger, representing the set in the released condition:

FIG. 20 is the cross-sectional view of the "Hudson" standard coupling body.

FIG. 21 shows the lower vies and the elevation of the internal cutting shaft and the external cutting body, showing the edge positioning;

Figure 22:
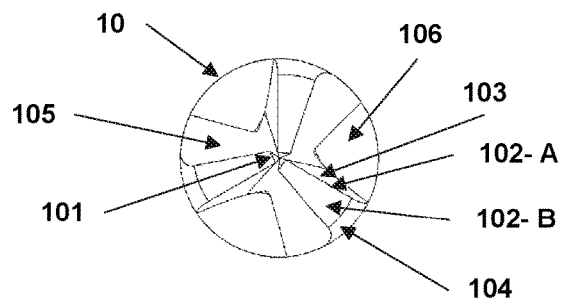
Figure 23:
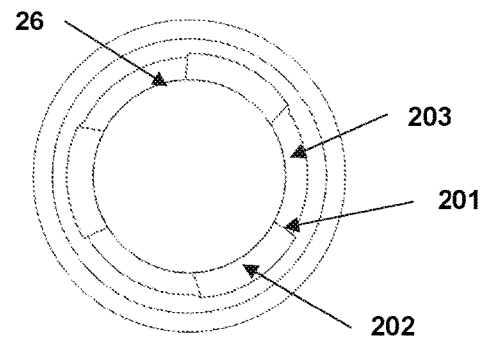
Figure 23:
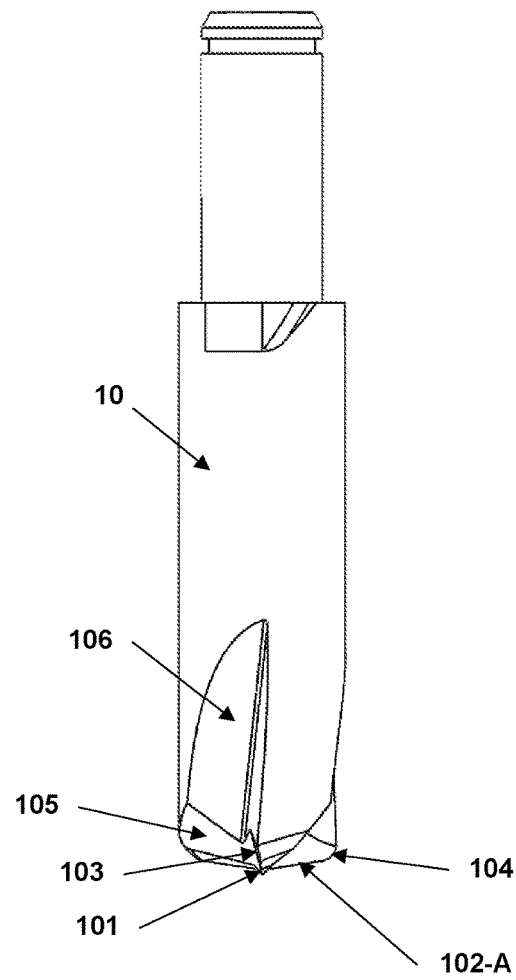
Figure 23:
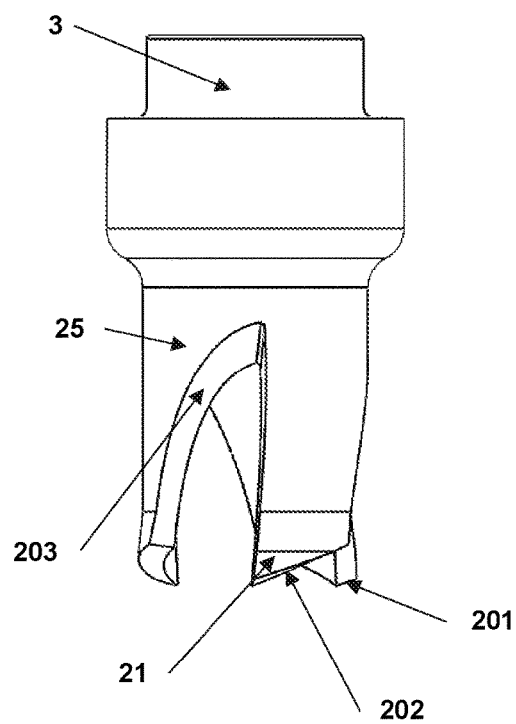

The set of FIG. 22 shows the lower view and the elevation of the internal cutting shaft edge:

The set of FIG. 23 shows the front view and the elevation of the internal cutting shaft edge.

DETAILED DESCRIPTION OF THE INVENTION

Figure 1:
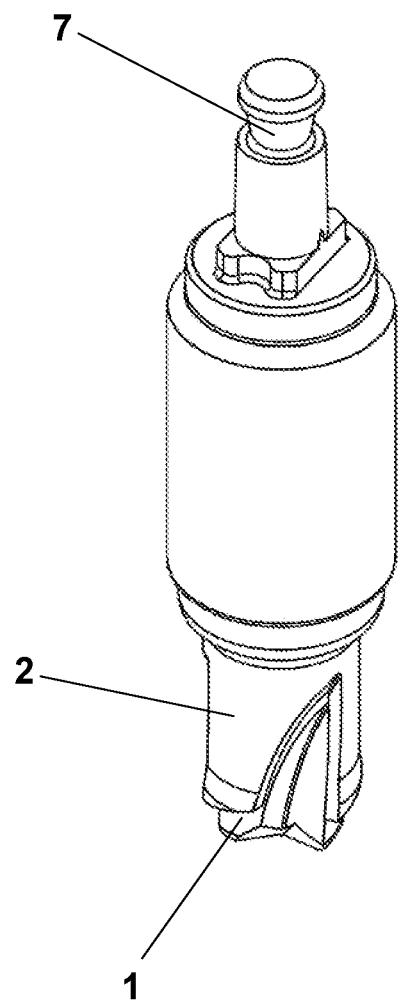
Figure 2:
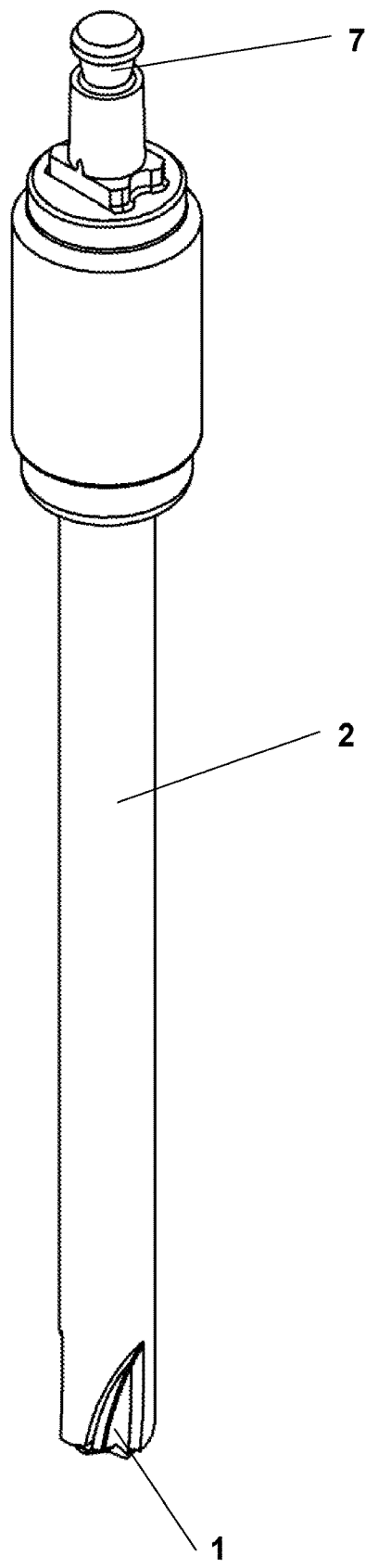
Figure 3:
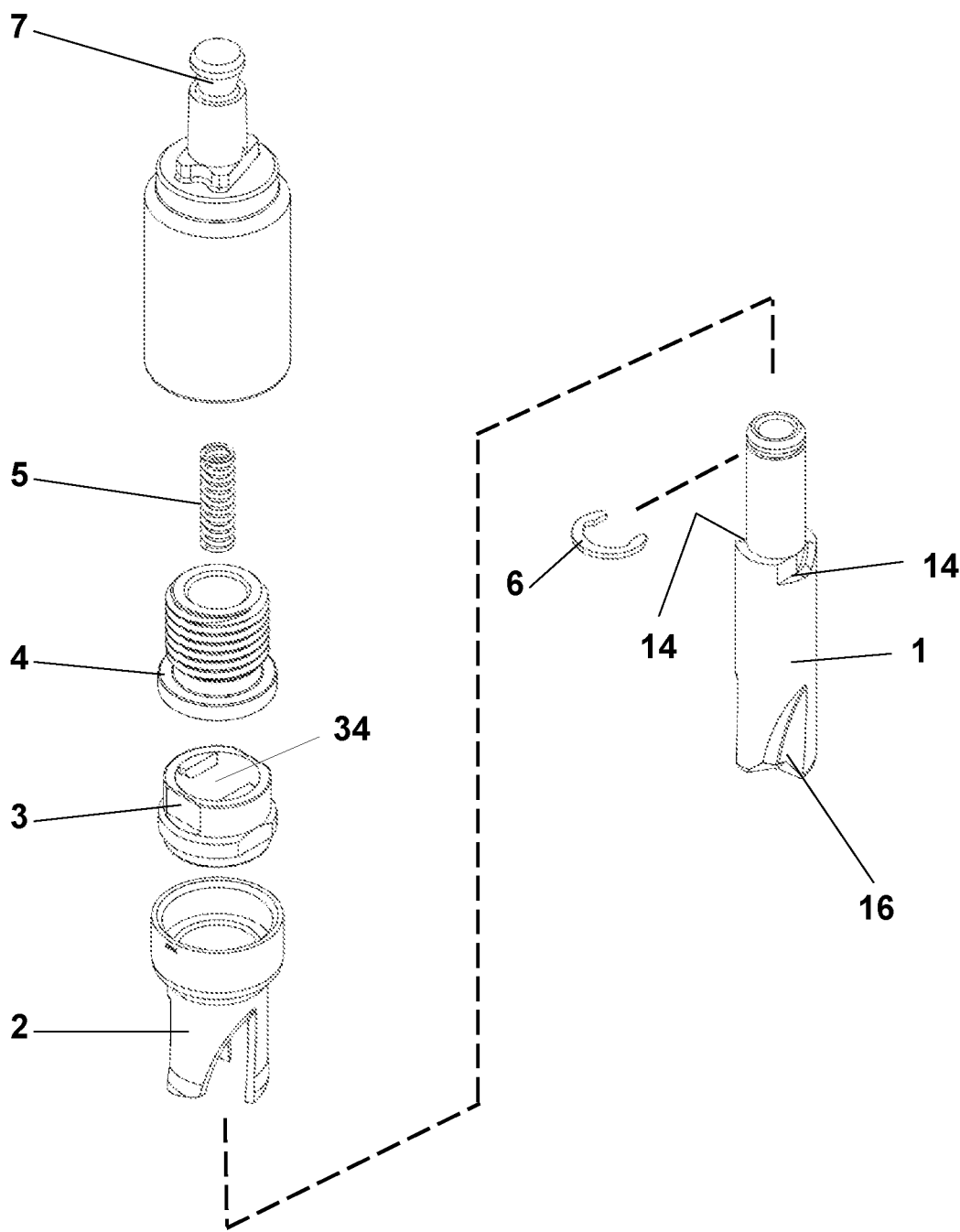
Figure 4:
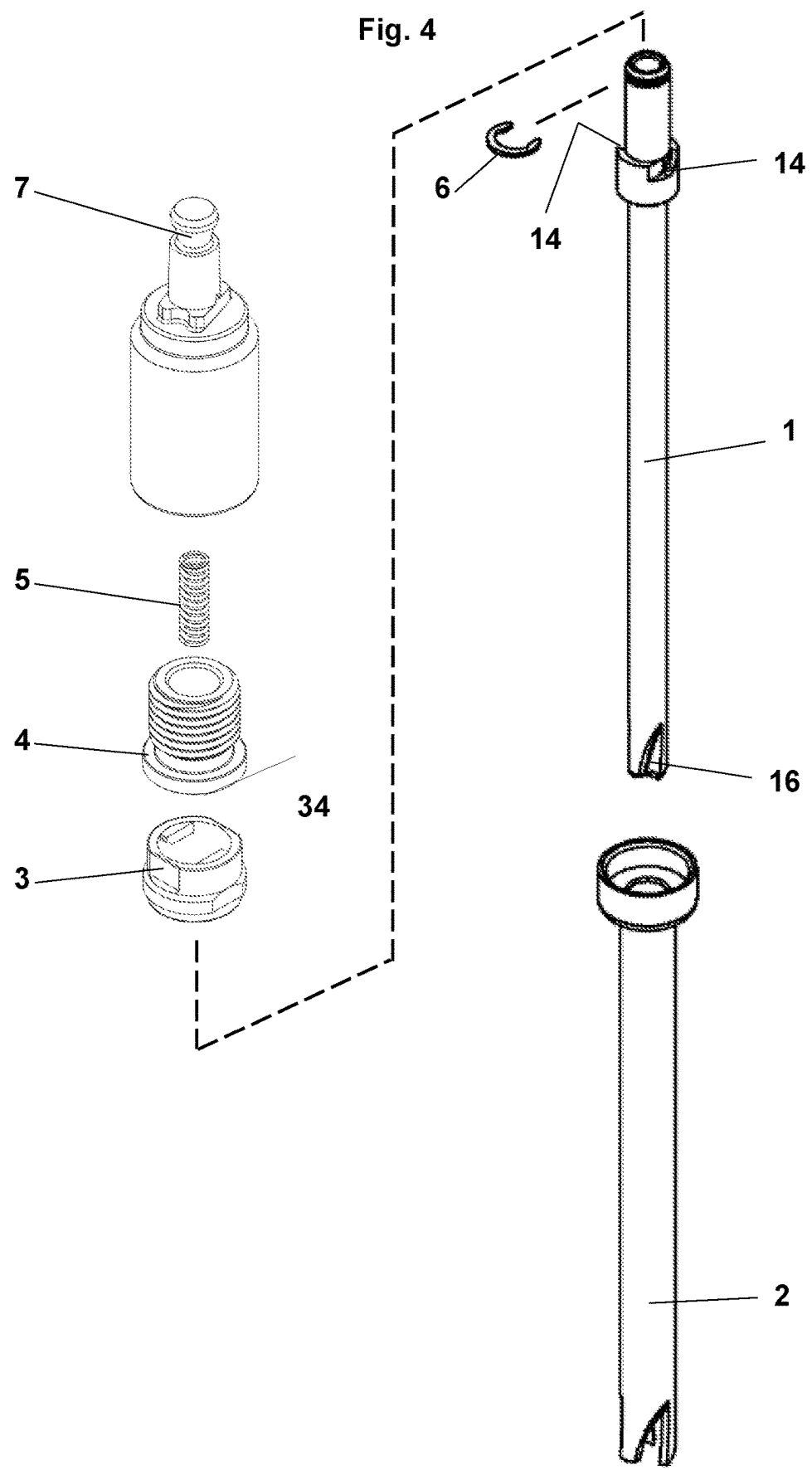

FIG. 1 shows the full assembly of the object of this proposal and FIG. 3 shows the exploded view of the pats comprising the referred set, which includes the internal cutting shaft [1], the external cutting body [2], the external body ring [3] the dragging trigger [4], the spring [5], the retention ring [6] and the "Hudson"-type coupling body [7]. FIG. 2 shows the full assembly of the long variant and FIG. 4 shows the exploded view of the long variant components with the same mechanical arrangement.

Figure 5:
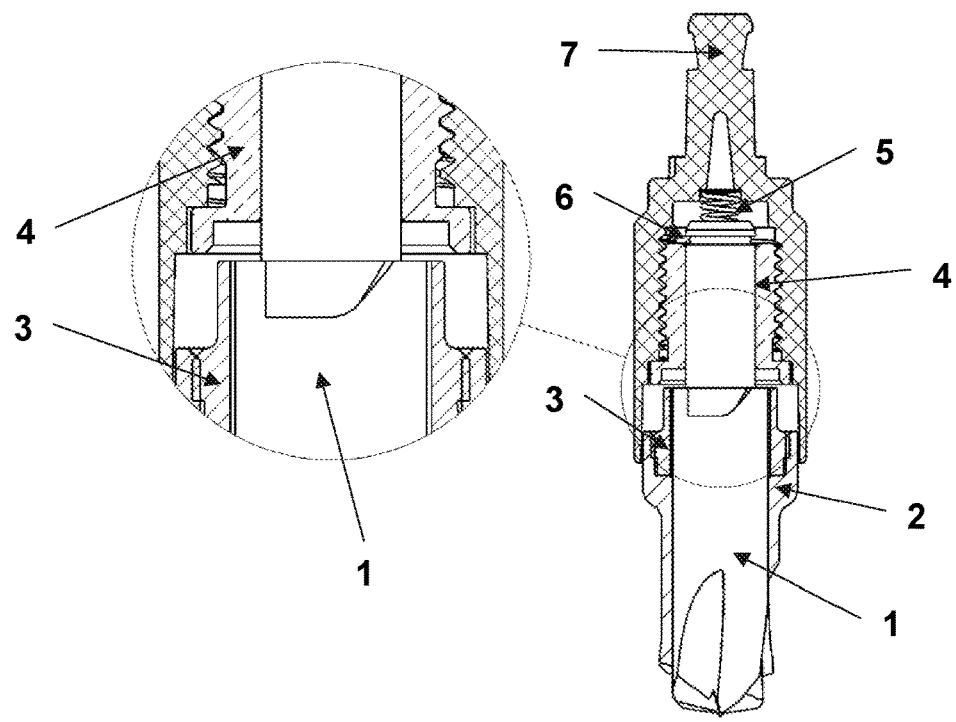
Figure 6:
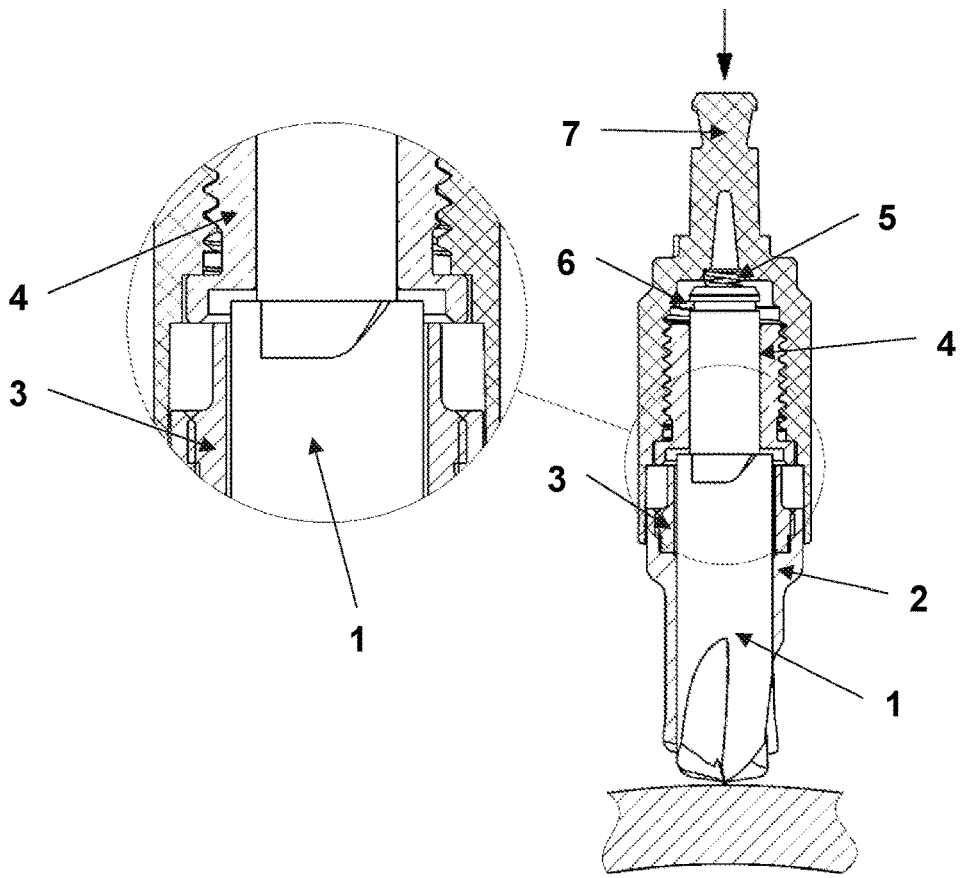
Figure 7:
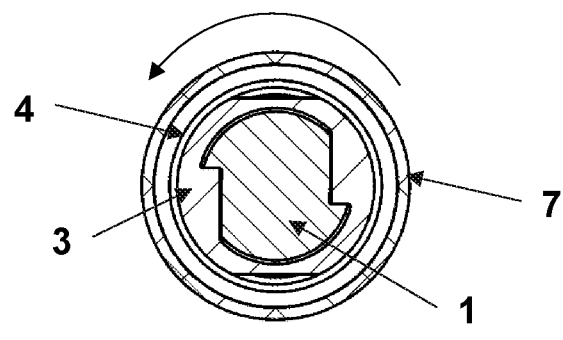
Figure 7:
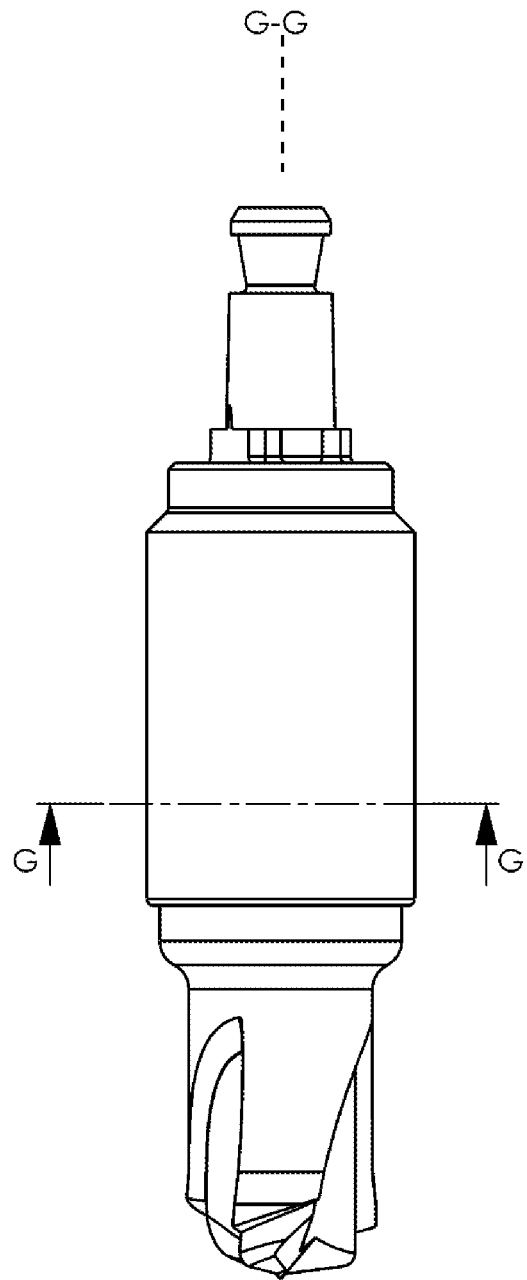

The assembly of the set is shown under two operating conditions. FIG. 5 shows the cross-sectional view of the drill bit assembly in the rest condition, i.e., in the released condition, where the internal cutting shaft [1] cams remain released from the dragging trigger [4], by means of the spring [5] pressure and the retention ring [6], what limits the movement between the internal cutting shaft [1] and the dragging trigger [4]. The internal cutting shaft [1] and the external cutting body [2] are assemble in such a way that the cutting geometry (G-G) of both remain aligned by the cam faces through the external body ring [3], as shown in FIG. 7 section. Such interaction allows that, when connecting the drill bit to a craniotome through the Hudson-type coupling body [7] and, pressing the cranial bone, as shown in FIG. 6, the internal cutting shaft [1] cams are coupled to the dragging trigger [4] housing.

The coupling movement is limited between the dragging trigger [4] lower face contact and the upper face of the external body ring [3]. Once the coupling is achieved, the craniotome rotary movement transmission is obtained, By overcoming the bone thickness, the internal cutting shaft [1] is released from the dragging trigger [4], assisted with the spring load [5].

Figure 8A:
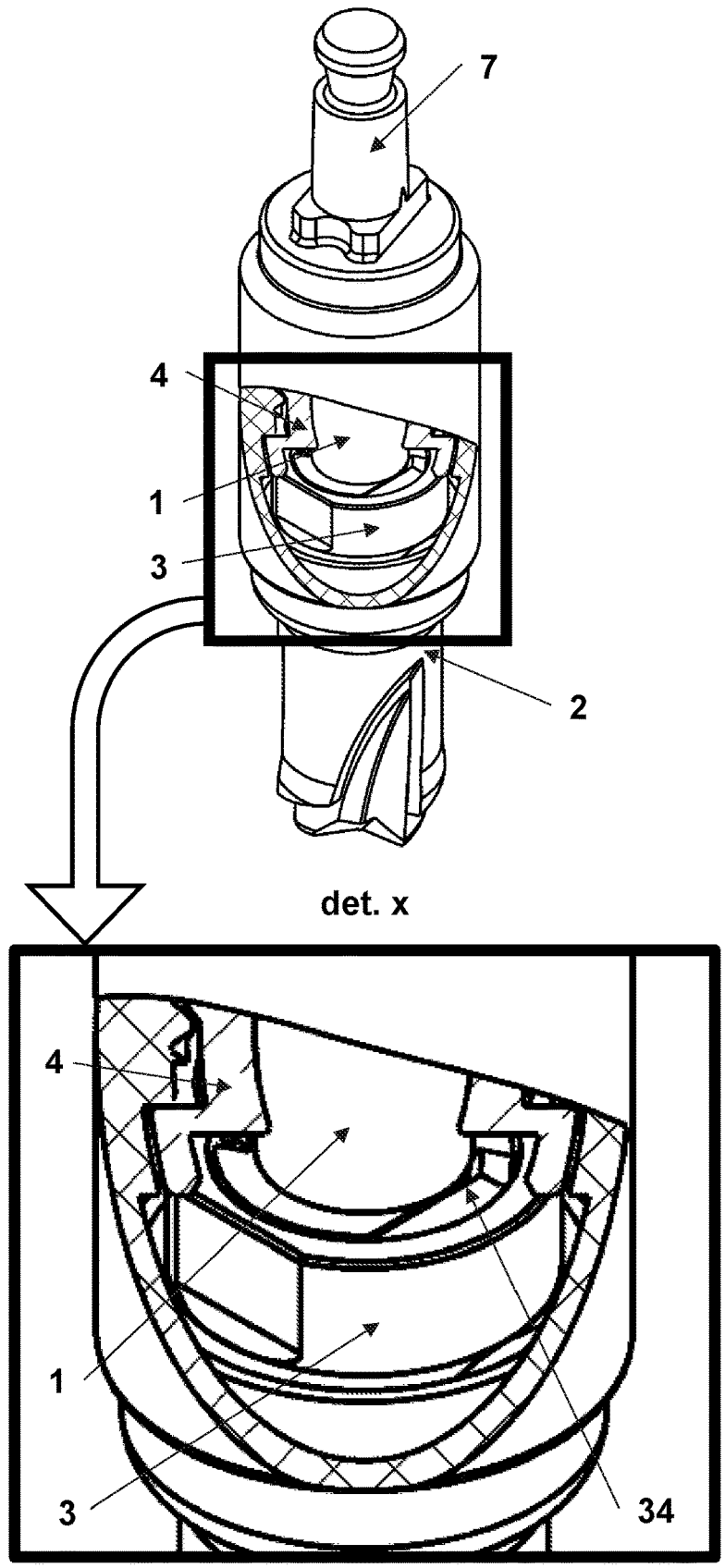
FIGS. 8a and 9a are enlarged details of portions of FIGS. 8 and 9 respectively
Figure 9A:
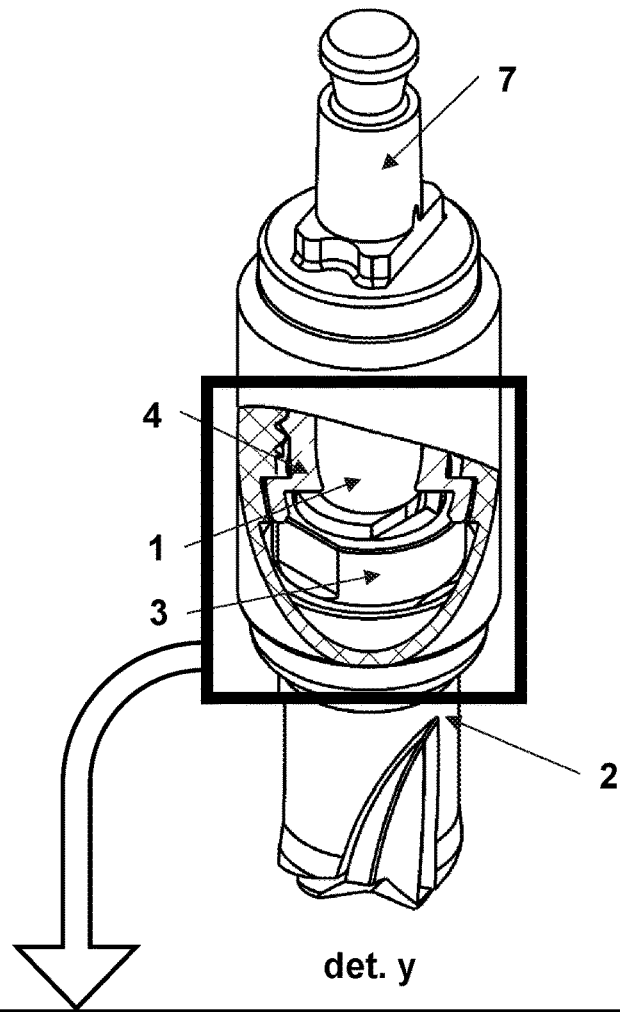
Figure 9A:
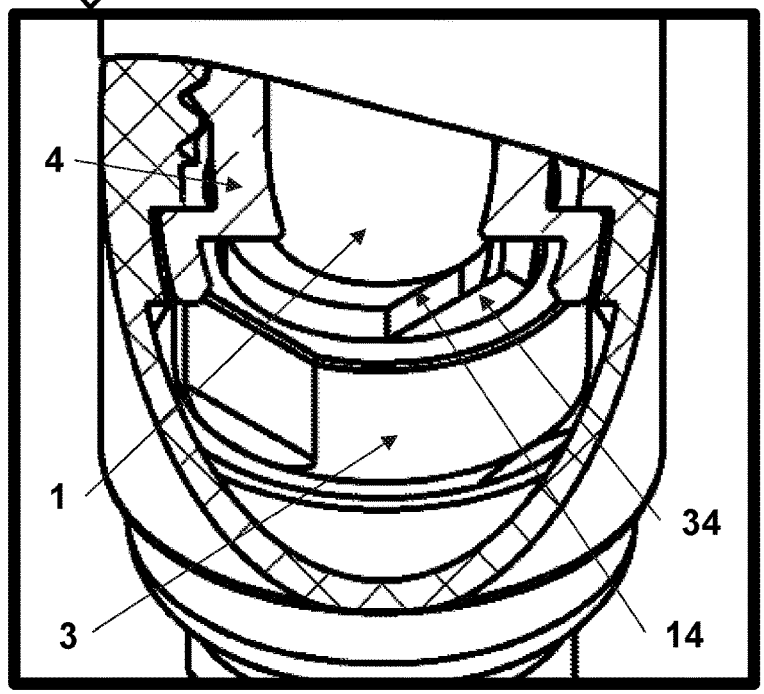

The internal cutting shaft [1] cams also slide, so that the upper face of the largest diameter of the internal cutting shaft [1] coincides with the upper face of the external body ring [3], with a small axial gap of approximately 0.4 mm between the dragging trigger [4] and the external body ring [3]. Thus, the internal cutting shaft [1], the external cutting body [2] and the external body ring [3] remain stuck on the bone, while the other components rotate falsely. This condition is presented in FIG. 8 and in FIG. 9 and shows the position of the internal cutting shaft [1] cams when the set is pressed and the cams coupled.

The result is a hole with two diameters, being one hole corresponding to the internal cutting shaft [1] diameter [10], which starts between the surface formed by the external cutting body [3], being that in the final portion of such hole a small bone disk is formed in order to help to protect the dura mater (known as "bone pad"); and a second lowered hole between the bone surface, until a distance which may range between 1 to 3 mm before the end of the first hole, corresponding to the external cutting body [2] diameter [21].

Figure 12:
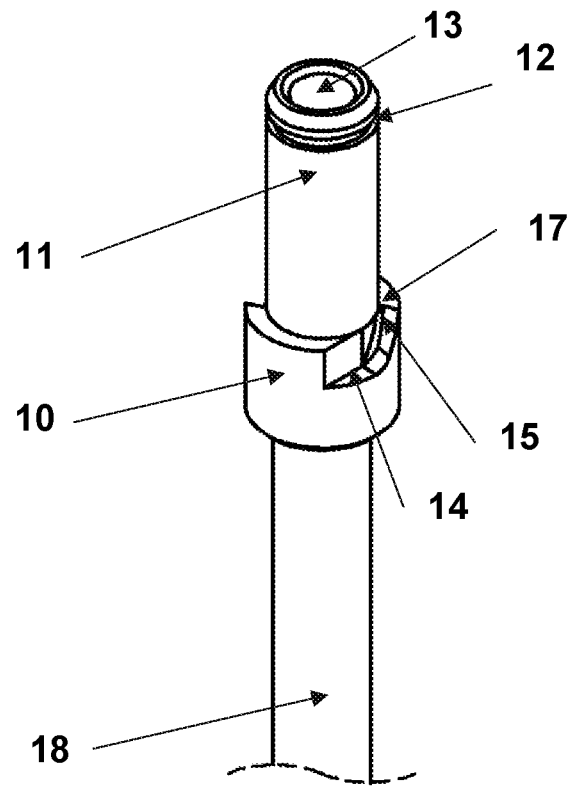
Figure 12:
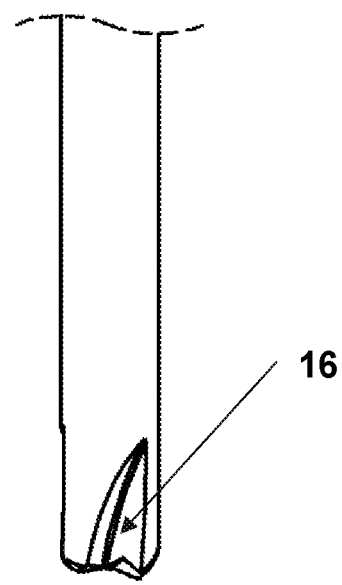

Concerning FIG. 1, below we depict the individual parts of the drill bit which will be described with more details. The internal cutting shaft [1], shown in FIGS. 10 and 11, comprises a shaft with two diameters [10] and [11], being that the largest diameter [10] presents the cutting profile [16] in one end, which will be described later on, and two cams opposed to each other, in the other end. Diameter [10] has a constant diameter or approximately 14 mm. FIG. 11 present the construction variant of the internal cutting shaft, which also presents a diameter [10] of approximately 14 mm, but with a length of approximately 9 mm from the upper face [17]. As shown in FIG. 12, from the lower face, the internal cutting shaft has a second diameter [18], which may range between 5 mm and 8 mm, with lengths between 25 mm and 130 mm, with the same cutting profile [16] shown in FIG. 11.

Each of the cams comprise two faces, being that one flat face [14] contacts the external body ring face [34], shown in FIGS. 13, 14, 15 and 16. Looking at FIGS. 8a/9a and their enlarged details X and Y, it can be observed that the faces [14] of the central drill cams are coupled—axially sliding—to the faces [34] of the ring [3]. This coupling takes place when the set is pressed against the skull and thus the central drill slides into the set and the pieces fit together; once the skull has been drilled, the central drill (no longer having contact resistance) slides forward, by the action of the spring [5] and the parts [14/34] disengage, leaving the central drill free (no longer rotates). The contact-coupling of the faces [14/34] ensures the alignment of the cutting geometries [16] and [24], shown in FIGS. 8/8a and 9/9a and X/Y details, allowing the drag of the rotary movement between the internal cutting axis [1] and the external cutting body [2]. One portion in faces [14] and [15] is exposed in approximately 1.2 mm and contact the dragging trigger face [42], shown in FIGS. 17, 18 and 19, being responsible for transmitting the craniotome rotary movement to the internal cutting shaft and to the external cutting body [2]. The other cam face [15] starts as a flat base and follows from the center with a helical upward slope of approximately 36 mm of pace to the face [17].

Said surface [15] contacts the external body ring face [35], shown in FIGS. 13, 14, 15 and 16 during drilling. When the bone thickness is overcame, the dragging occurs between them allowing the release, as shown in FIGS. 13, 14, 15 and 16. The largest diameter [10] serves as a guide for the part [2] hole [26], shown in FIGS. 13 and 14. The smallest diameter [11] serves as a guide for the dragging trigger hole [41], shown in FIG. 17. The upper end of the part [1] is provided with a groove [12], where the retention ring [6] is assembled. Such ring limits the movement between the dragging trigger [4] and the external body ring [3] during the drill bit coupling and release, shown in FIGS. 18 and 19 and, more specifically, it limits the groove [12] of FIGS. 10, 11 and 12, the external body ring face [36] of FIG. 8 and the dragging trigger faces [44] and [46] in FIG. 17.

The upper face of the internal cutting shaft [1] is provided with a hole [13] which serves as a housing for the spring [5].

Figure 13:
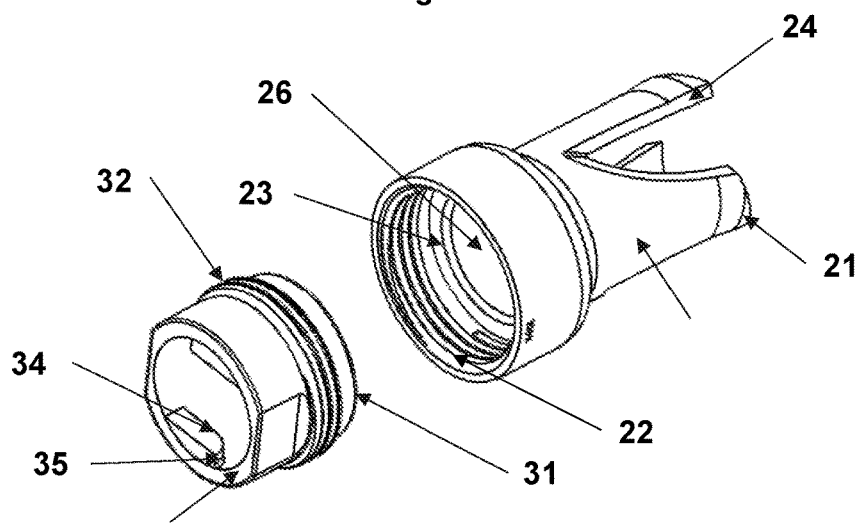
Figure 15:
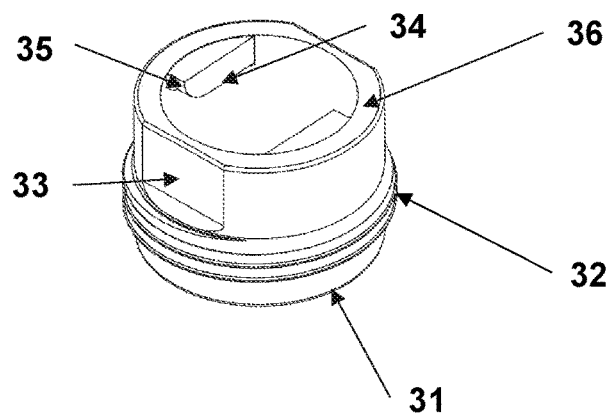
Figure 16:
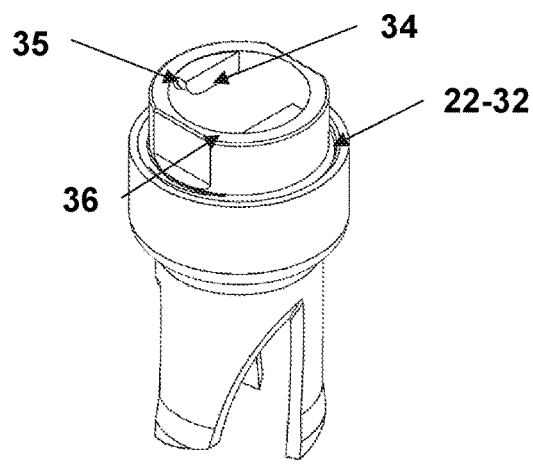

The external cutting body [2] is assembled with the external body ring [3], forming a subset, as shown in FIGS. 13, 15 and 16. The external cutting body has a hole [26], where the internal cutting shaft [1] is assembled by means of a thread [22] in the upper end where the external body ring thread [32] is assembled and a flat seating surface [23] of the external body ring in the face [31]. The ring can be fixed by means of a spanner in the flat faces [33]. The other end is provided with the cutting profile [24] and a diameter [21] measuring between 9 and 14 mm and length of approximately 20 mm, which includes a recess [25], the role of which is to reduce the lateral friction during the drilling operation of thicker bones.

Figure 14:
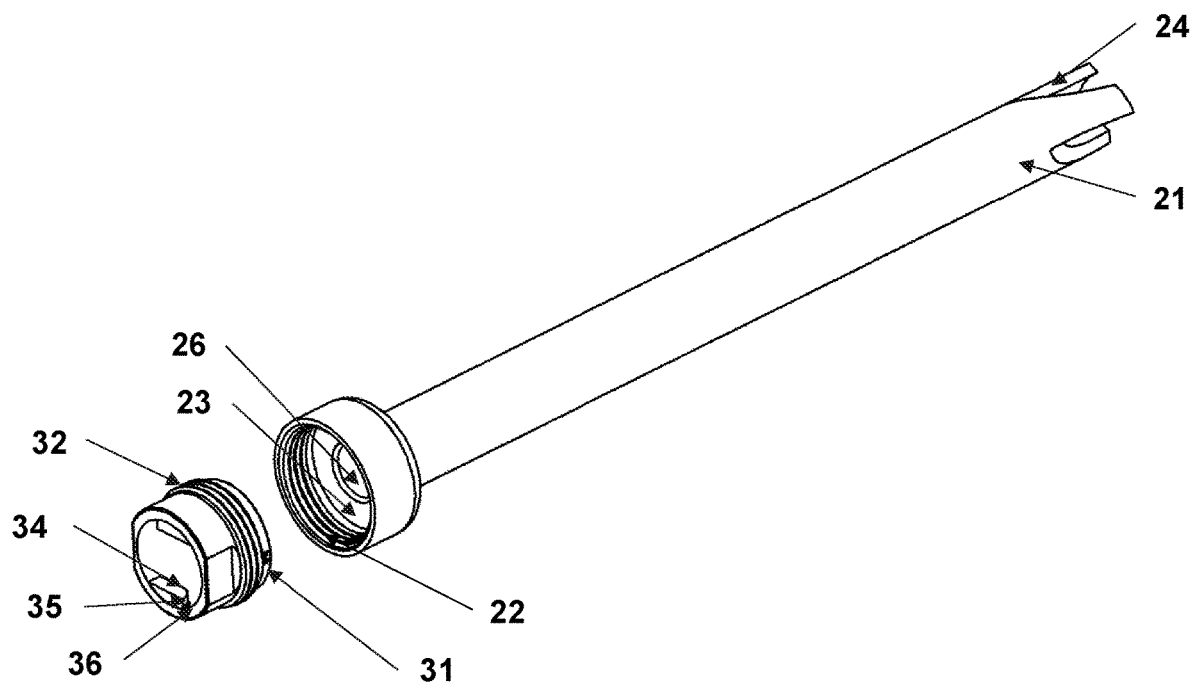

The long construction variant shown in FIG. 14 has a diameter [21] measuring between 9 mm and 12 mm with a length of approximately 120 mm. Another difference in the long variant shown in FIG. 14, compared to FIG. 13, is that the recess [25] is not present, because the diameter [21] will serve as a guide to be used in stereotaxic instruments or surgical robots.

Figure 17:
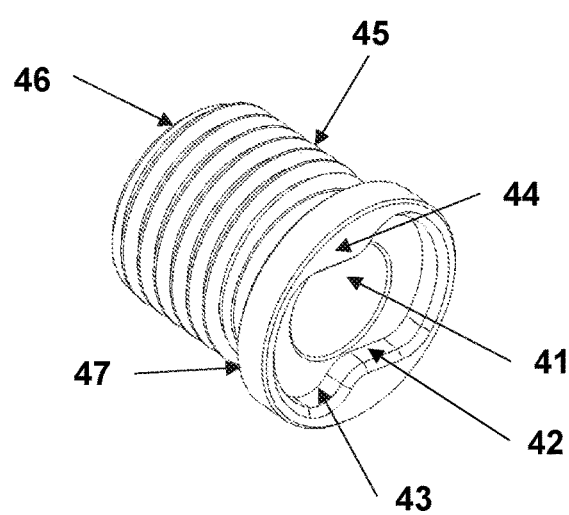
Figure 18:
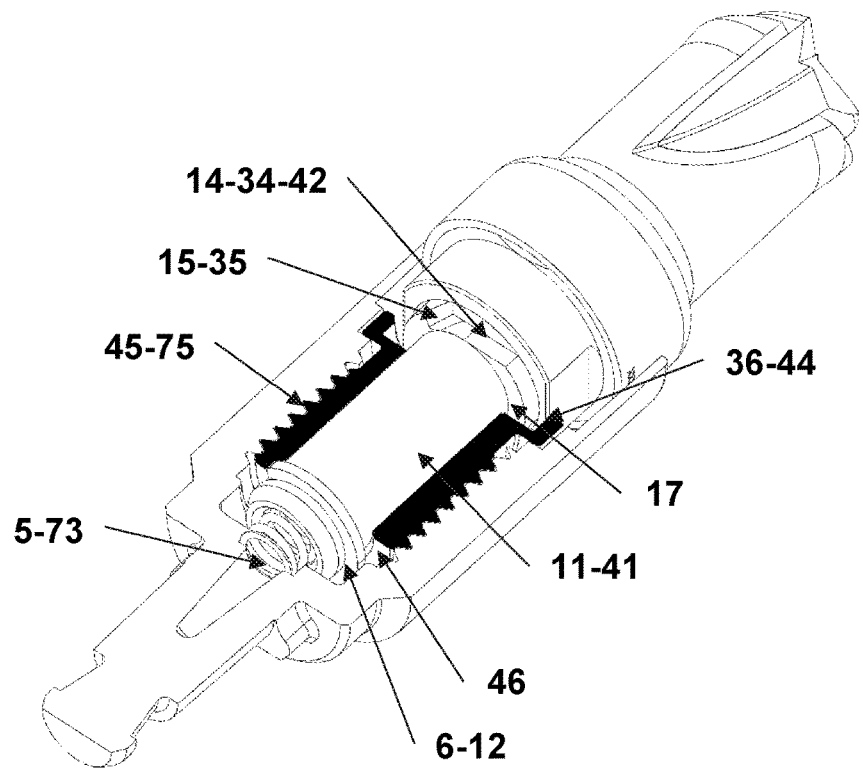
Figure 19:
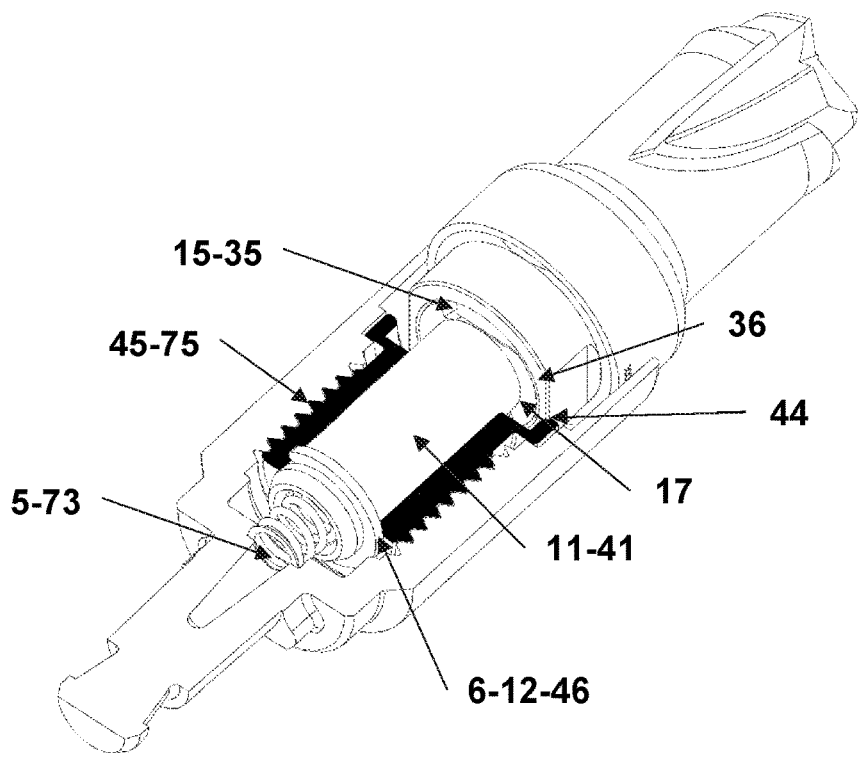

As previously shown the dragging profile of the cams is formed by protrusions 34/35 (FIG. 15) and interact with cams [14] and [15], shown in FIGS. 10, 11 and 12 and which also interact with protrusion [42] (FIG. 17) in the drill bit coupling and releasing mechanism, shown in FIGS. 18 and 19.

The dragging trigger [4] is a metal sleeve, made of bronze, formed by hole [41] (FIG. 17) with sliding adjustment between the latest and diameter [11] of the internal cutting shaft [1] (FIGS. 10, 11 and 12). It is provided with a housing [42] and [43] where internal cutting shaft [1] cam faces [14] contact to couple and release the set during the drilling operation.

The lower face [44] remains in contact with the upper face [36] of the external body ring, when the set is coupled during the drilling operation. In the condition that the drill bit is released, face [46] remains in contact with the retention ring [6]. It is provided with a thread [45] which is assembled in thread [74] in the Hudson-type coupling body [7] (FIGS. 17 and 20).

The entire drill bit coupling and releasing mechanism of this proposal is encapsulated in the plastic Hudson-type coupling body [7]. It has a body [71], where the coupling device is mounted in the craniotome, being that the coupling device model may range according to the craniotome by other manufacturers, such as the Smith-type coupling device, for example. Diameter [72] serves to cover the external body ring [3], the upper part of the external cutting body [2] and the two cams formed by [14], [15] and [17] (FIGS. 11 and 12). Spring [5], mounted in part [1] housing [13] (FIG. 1), is also supported on the coupling body housing [73] (FIG. 20), so that it may have enough load to assist in releasing the drill bit cams, shown in FIGS. 18 and 19.

Figure 20:
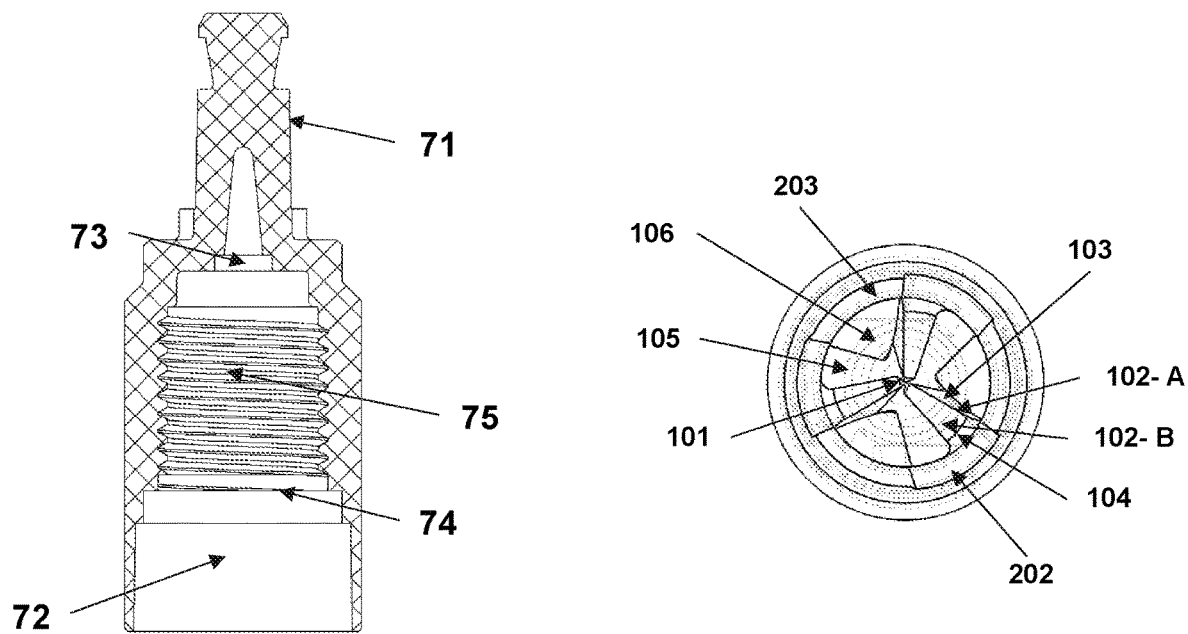

As previously mentioned, thread [75] is assembled with the dragging trigger [4] thread [45] and its seating in Hudson-type coupling device [7] is performed by the contact between the faces [47 and 74] (FIGS. 17 and 20).

As previously described, the internal cutting shaft [1], shown in FIGS. 10 and 11, comprises a shaft provided with two diameters [10 and 11], being that the largest diameter [10] is provided with the cutting profile [16] in one end, as shown in FIGS. 11 and 13 and the external cutting body [2] cutting profile [24].

It has also been described that the interaction between the external body ring [3] faces [34 and 35] ensures the alignment of the cutting geometries [16 and 24], shown in FIGS. 15 and 16 and allows the rotary movement dragging between the internal cutting shaft [1] and the external cutting body [2].

Figure 21:
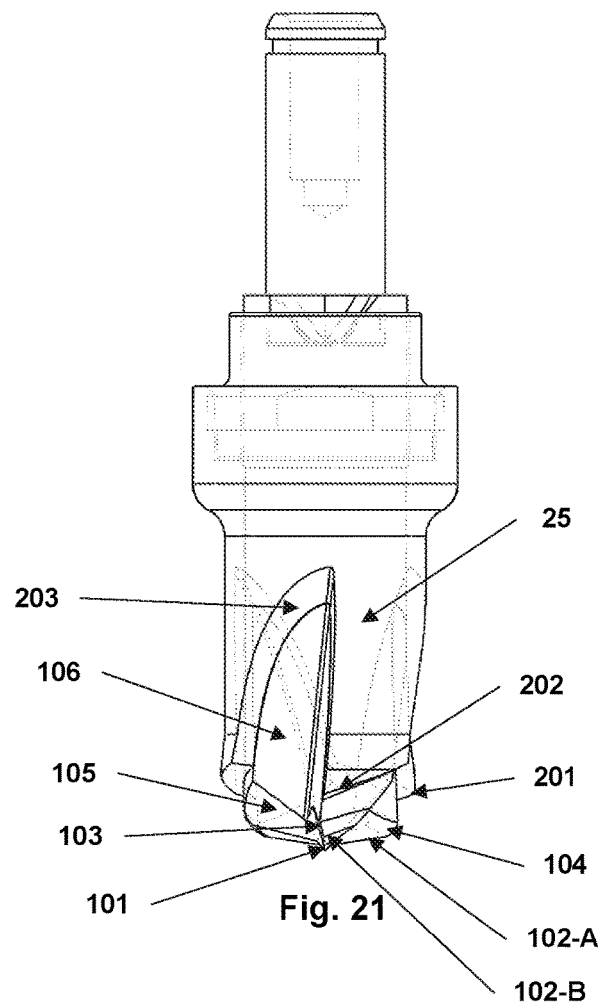

The set in FIG. 21 shows the assembly in the coupled condition between the internal cutting shaft [1], the external cutting body [2] and the external body ring [3], where the alignment of the departure angles formed by [106] and [203] is identified. There's also a distance between the point angle [102] edge and the point angle [201], which may range between approximately 1 and 3 mm. The desired alignment and positioning are obtained by the fact that the sharpening process is conducted with the set assembled. FIGS. 15, 16, 17 and 18 show the lower and front views of the internal cutting shaft [1] and the external cutting body [2].

Starting, with the internal cutting shaft [1], this is formed by the body [10], the cut of which results in the smallest diameter of the hole. As shown in the set of FIGS. 22 and 23, the internal cutting shaft comprises a tip 101 of 0.4 mm, which allows the drill bit to remain positioned to perform the hole. The cutting geometry id formed by the point angle [102-A] of approximately 7° from the base, between the point edge [101] to the face [10], with a clearance angle [102-B] of approximately 20° from the base.

From the point [101], we have a facet [103], the angle of which is negative in approximately 15° with respect to the drill bit shaft. The edge formed between the intersection of angles [102-A], [102-B] and [103] has a rounding [104], so as to soften the internal cutting shaft cut [1] (set of FIG. 21) and the formation of the bone disc, known as "bone pad". There's also a second faceted corner [105], perpendicular to the facet [103] and with an angle of approximately 40° from the shaft, which decreases the clearance angle [102-B] contact area, favoring the release of chips (see elevation in FIG. 22). Concerning the release of chips, there's also the geometry of the departure angle [106] and [206], with a slope of approximately 6° with respect to the internal cutting shaft [1] center line (FIGS. 21, 22 and 23).

As shown in FIGS. 21 and 22, the departure angle faces [106] and [203] profile form an angle of approximately 75°. This profile describes an arc trajectory [16], shown in FIGS. 10, 11 and 12, starting from the internal cutting shaft [1] end [101] and ending in the external cutting body [2] recess face [25], in a vertical distance of approximately 20 mm (FIGS. 21, 22 and 23).

As shown in FIG. 21, the sharp faces are positioned at 1200 between them, forming the tip profile [101] and a minimum frame diameter of approximately 4 mm in the internal cutting shaft [1]. The result of this positioning is a higher volume to release the chips, allowing to reach bones with higher thicknesses.

The external cutting body [2] is formed by two diameters [21 and 25] (FIG. 23). Diameter [21], the cut of which results in the lowered hole diameter, has a recess [25] (FIG. 23), the role of which is to reduce the lateral friction during the drilling of thicker bones. It's important to emphasize that, as previously described and shown in FIG. 14, the long construction variant is not provided with the recess [25], because the diameter [21] may be coupled to stereotaxy-driven instruments or in surgical robots, guaranteeing increased precision in the drilling trajectory.

As shown in FIG. 23, the geometry is formed by the point angle [201] of approximately 15° from the base, between the inner diameter [26] and the outer diameter [21], having a clearance angle [202] of approximately 20°, in parallel with the clearance angle [102-B] of the internal cutting shaft [1] (FIG. 21).

As previously described, the departure angle [203] is formed in combination with departure angle [106] (FIG. 21) so that, during the drilling operation, the surfaces formed by [106] in the internal cutting shaft [1] and [203] in the external cutting body [2] coincide. The characteristics of the described sharpening, cutting angle, point angles and clearance angles geometries, also apply for the long construction variant.

The invention claimed is:

1. Release System and Cutting Profile applied to disposable self-locking intracranial drill bit comprising:
  a cutting shaft having a drill bit at one end and cams proximate to an other end,
  an external ring having internal faces that interact with said cams and external surfaces,
  a bushing configured to fit within a spring-containing housing and having internal surfaces configured to interact with external surface of the external ring, wherein said cams on the cutting shaft comprise flat faced cams and a helically faced cam located between the flat faced cams, and
  a dragging geometry is effected by opposed cams and surfaces, configured to interact while the drill bit experiences resistance to forward movement and to disconnect when the drill bit experiences no resistance to forward movement, by an action of a spring on the external ring thereby ending connections between the cams mounted on the cutting shaft and the surfaces of the external ring and cooperating internal surfaces of the bushing.

2. The Release System and Cutting Profile as claimed in claim 1, wherein the cutting shaft comprises:
  an internal cutting shaft, presenting two diameters, wherein a largest diameter presents a cutting profile at one end and integrated cams proximate to an other end, said internal cutting shaft serving as a guide to a coupling and releasing mechanism; and
  an external cutting body mounted with a threaded ring, which causes an interaction with the internal cutting shaft cams, and
  a retaining ring fixed to a smaller diameter of the internal cutting shaft, conveys a rotary movement of the bushing to the cutting shaft prior to decoupling.

3. The Release System and Cutting Profile applied to disposable self-locking intracranial drill bit, according to claim 2, wherein a combination between the internal cutting shaft and the external cutting body departure angle profiles, in combination with faces of the cams and faces of the external ring, applied to a clearance angle in the internal cutting shaft, in combination with an external cutting body recess, are configured to facilitate decoupling of a rotary drive mechanism from the cutting shaft.

4. The Release System and Cutting Profile of claim 1, wherein said housing within which the spring is mounted is a Hudson-type coupling.

* * * * *